United States Patent [19]
Wolfangel

[11] 3,962,412
[45] June 8, 1976

[54] METAL HYDROXIDE MICROSPHEROIDAL SCINTIGRAPHIC AGENTS AND METHOD OF PREPARATION
[75] Inventor: Robert G. Wolfangel, St. Louis, Mo.
[73] Assignee: Mallinckrodt Chemical Works, St. Louis, Mo.
[22] Filed: June 11, 1973
[21] Appl. No.: 368,864

[52] U.S. Cl. ............................. 424/1; 252/301.1 S; 250/303
[51] Int. Cl.² ....................................... A61K 43/00
[58] Field of Search ................ 424/1; 252/301.1 R, 252/301.1 S ; 423/93, 142

[56] References Cited
OTHER PUBLICATIONS

Webber, M. et al., Demonstration of Thrombophlebitis and Endothelial Damage by Scintiscanning, Radiology, vol. 100, July, 1971, pp. 93–97.
Darter, E. et al., Improved Binding and Stability of 99m Tc–Iron Hydroxide, In J. Nuclear Medecine 12: pp. 632–643, Sept. 1971.
Yano, Y. et al., 99m Tc–Ferric Hydroxide Macroaggregates for Pulmonary Scintiphotography, In J. Nuc. Med. 10: pp. 683–686, Nov. 1969.
Zolle, I. et al., Preparation of Metabolizable Radioactive Human Serum Albumin Microspheres for Studies of the Circulation, In Int. J. App. Rad. and Iso. 21: pp. 155–167, 1970.

*Primary Examiner*—Benjamin R. Padgett
*Assistant Examiner*—R. E. Schafer
*Attorney, Agent, or Firm*—Koenig, Senniger, Powers and Leavitt

[57] ABSTRACT

Metal hydroxides such as $Fe(OH)_2$, $Fe(OH)_3$ and $Sn(OH)_2$ are prepared in the form of spherical particles of uniform and controlled size suitable for tagging with a radioactive element such as technetium-99m. Aqueous suspensions of such tagged particles are useful in scintigraphy as lung scanning agents.

3 Claims, 2 Drawing Figures

METAL HYDROXIDE MICROSPHEROIDAL SCINTIGRAPHIC AGENTS AND METHOD OF PREPARATION

BACKGROUND OF THE INVENTION

1. Field of the Invention

The present invention is directed to the field of radiodiagnostic agents and more particularly to scintigraphic agents.

2. Description of the Prior Art

Aqueous suspensions of various metallic hydroxides such as $Fe(OH)_2$, $Fe(OH)_3$ and $Sn(OH)_2$ tagged with a radionuclide such as technetium-99m have been used to obtain perfusion lung scintigraphs which provide significant diagnostic information describing circulatory defects within the lungs. Suspensions used for lung scintigraphy must be tagged with a short lived gamma-emitting radionuclide and also be within a prescribed size range distribution. Pulmonary lung scintigraphy is based upon physical entrapment of radioactive particles within the capillary and terminal arterial network of the lungs. The anatomy of the pulmonary system requires that the particles be greater than $10\mu$ in diameter in order for entrapment to occur but particles greater than $100\mu$ are to be avoided because they would tend to occlude major arterioles and thus present a potential hazard.

Metallic hydroxide suspensions for this purpose have previously been prepared by admixing an aqueous solution containing a hydrolyzable salt of the metal and a compound of the radionuclide with a solution of a strong base such as sodium hydroxide under carefully controlled conditions. The precipitated metal hydroxide thereby acts as a collector and carrier for the radionuclide. Even under the most carefully controlled conditions, this method yields at best a suspension of irregularly shaped particles, a significant percentage of which are generally either too small or too large. There has been an unfulfilled need, therefore, for an improved method for preparing metallic hydroxide suspensions containing particles which are substantially spherical and which have diameters within the desired range of $10\mu$ and $100\mu$.

SUMMARY OF THE INVENTION

Among the objects of the present invention may be noted the provision of improved metallic hydroxide suspensions for use as scintigraphic agents; the provision of suspensions of the character described in which the particles are substantially spherical with diameters between $10\mu$ and $100\mu$; and the provision of methods for preparing suspensions of the character described. Other objects and features will be in part apparent and in part pointed out hereinafter.

Briefly, the present invention comprises directing an aerosol mist containing a hydrolyzable salt such as a chloride of the desired metal onto the surface of a stirred solution of a strong base. The particles of metallic hydroxide are thereby precipitated in the form of spheres at impact of the mist droplets on the liquid surface with the particles having diameters between approximately $10\mu$ and $100\mu$. Aqueous suspensions of these spheres may be stored indefinitely and then tagged with a radionuclide at some later time to form radioactive compositions for use in scintigraphy.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

In accordance with the present invention, it has now been found that metal hydroxides in the form of substantially spherical particles having diameters between approximately $10\mu$ and $100\mu$ may be conveniently prepared by converting a solution of a hydrolyzable salt of the metal into an aerosol mist and directing the mist into a vessel substantially filled with a stirred solution of a strong base and a wetting agent.

The hydrolyzable metal salt present in the aerosol mist is preferably a chloride such as $FeCl_3$, $FeCl_2$, $SnCl_2$, etc. However, chloride may be replaced by other anions such as nitrates, sulfates, acetates, and the like.

Various means may be employed for generating the aerosol mist. For example, a compressed air sprayer made from corrosion-resistant material or similar atomizer can be used. The size of the mist droplets may be controlled by varying the size of the orifice and/or the air pressure.

Figure 1:
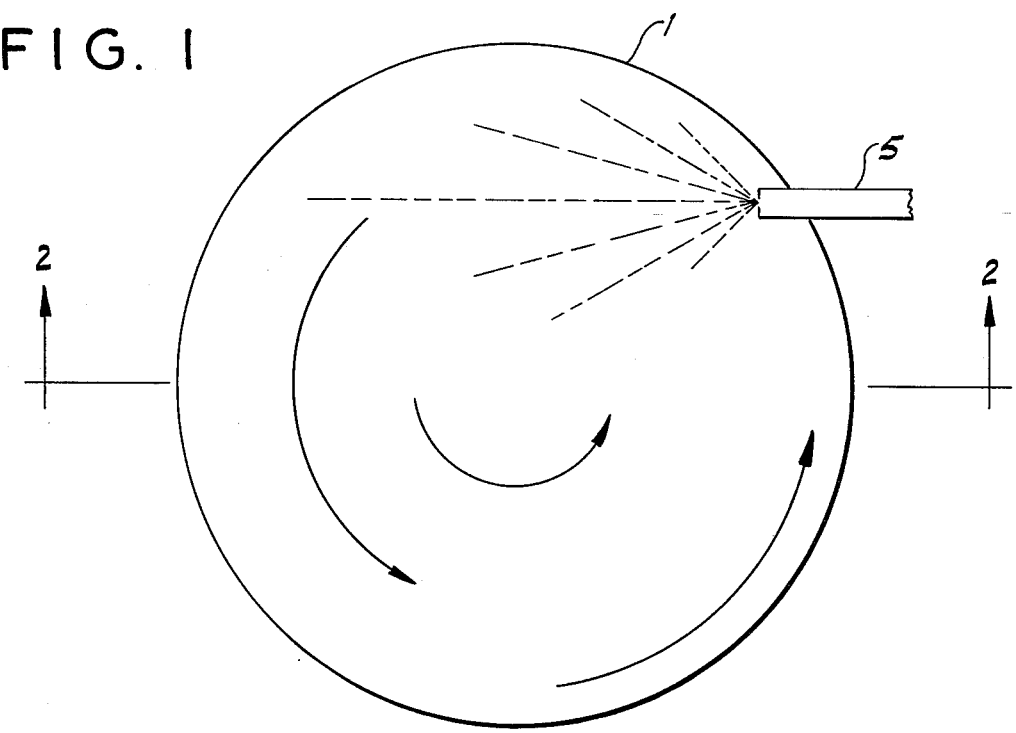
FIG. 1 is a top plan view of an atomizer-bath arrangement used in carrying out the method of the invention.
Figure 2:
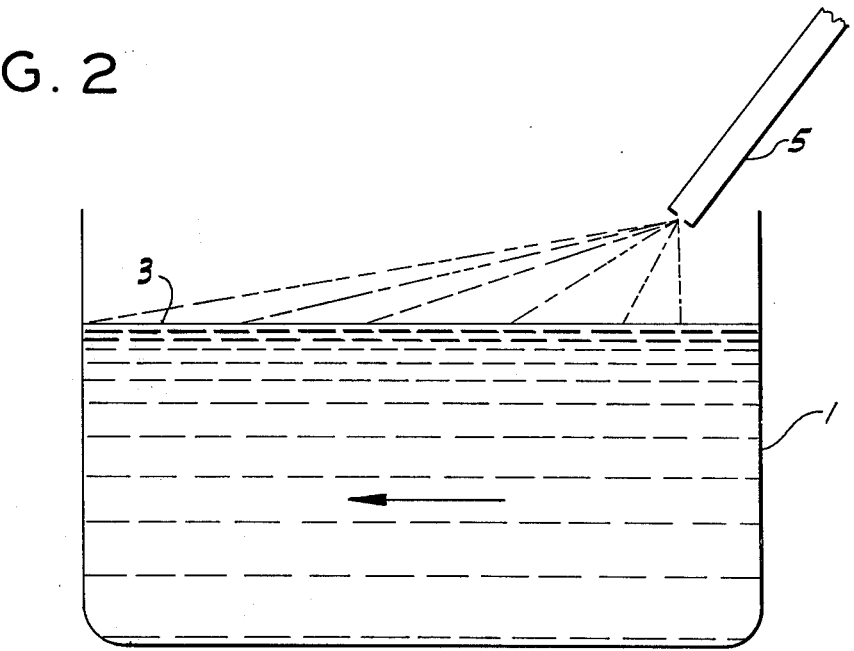
FIG. 2 is a vertical cross section taken on line 2—2 of FIG. 1.

FIGS. 1 and 2 illustrate the preferred physical conditions for carrying out the invention. A cylindrical vessel 1 contains a solution 3 of a strong base such as sodium hydroxide, potassium hydroxide or other alkali metal hydroxide. As shown, the nozzle 5 of an atomizer (not shown) is preferably tilted with respect to the bath of vessel 1 and the aerosol mist is thereby directed toward the sodium hydroxide or strong base solution so that the mist droplets strike the surface of the bath at an angle between about 10° and 90°. The bath is also slowly stirred so that it is moving in a direction parallel with the direction of the mist as shown in FIG. 1.

The size and shape of the metal hydroxide particles obtained can be varied by regulating the spray pressure, orifice size of the atomizer, angle of incidence and/or the concentration of the hydrolyzable metal salt solution used to generate the aerosol mist so that the particles are generally spherical in shape and have diameters between $10\mu$ and $100\mu$. It will be recognized that the particle size of the metal hydroxide particles is proportional to the size of the mist droplets and the conditions necessary to produce metal hydroxide particles of the desired shape and particle size may be readily determined empirically by routine experimentation.

The surface tension of the strong base or sodium hydroxide solution is also preferably lowered to facilitate penetration of the droplets. This is accomplished by adding a suitable wetting agent for which purpose a lower aliphatic alcohol such as methanol, ethanol, propanol and the like or other conventional wetting agent is effective.

Shortly prior to use in scintigraphy, the metal hydroxide spheres are tagged with a radio-nuclide such as technetium-99m or iron-59. This is simply and effectively accomplished by adding to an aqueous suspension of the spherical particles a solution of a compound containing the desired radionuclide, e.g., sodium pertechnetate-99m such as may be obtained from a commercially available technetium-99 generator. In the latter case, it is preferable to add also a tagging agent which may be a solution of $SnCl_2$ in dilute hydrochloric acid. A tagging agent is, however, unnecessary in the case of iron-59. After the spherical particles are tagged with the radionuclide, they may be washed by decantation and resuspended in distilled water or preferably physiological saline solution.

While technetium-99m and iron-59 are ordinarily the preferred radionuclides for scintigraphy, if desired the spherical particles of the present invention may also be tagged with other radionuclides such as for example indium-111 or indium-113$^m$.

The following example illustrates the invention:

EXAMPLE

A receiving bath consisting of 200 ml. of 5 N. sodium hydroxide, 500 ml. methanol and 1300 ml. distilled water was placed in a 2000 ml. crystallizing dish. The bath filled the dish to the brim and was gently stirred so that it slowly revolved. An aerosol mist of a freshly prepared 1% $FeCl_3$ solution was directed onto the surface of the bath at an angle between about 10° and 90° as shown in the drawings. The mist was generated using an atomizer powered by compressed air.

From 1 to 100 ml. of the $FeCl_3$ solution can be aerosolized into the receiving bath. When aerosolization is complete, the particles can be washed by decantation and resuspended in distilled water to form a 1% suspension. The spray pressure, orifice size of the atomizer, angle of incidence and the concentration of the $FeCl_3$ solution were such that the metal hydroxide particles obtained were generally spherical in shape and ranged between $10\mu$ and $100\mu$ in diameter.

The particles of $Fe(OH)_3$ were tagged with technetium-99m as follows: To 1 ml. of the suspension is added 0.1 ml. of a solution containing 4 mg./ml. of $SnCl_2.2H_2O$ in 0.1 N. HCl and this was followed by 5 ml. of eluate from a commercial technetium-99m generator. The tagged particles were then washed by decantation and resuspended in physiological saline solution.

As indicated above, when it is desired to tag the particles with iron-59, it is only necessary to add a solution of radioactive $FeCl_3$ to the iron hydroxide suspension. The addition of tin is not necessary. The tagged particles are then washed by decantation and resuspended in physiological saline solution as before.

In view of the above, it will be seen that the several objects of the invention are achieved and other advantageous results attained.

As various changes could be made in the above methods and products without departing from the scope of the invention, it is intended that all matter contained in the above description or shown in the accompanying drawing shall be interpreted as illustrative and not in a limiting sense.

What is claimed is:

1. A composition for use as a scintigraphic agent comprising an aqueous suspension of substantially spherical particles of an insoluble metal hydroxide tagged with a radionuclide, said particles having diameters between approximately $10\mu$ and $100\mu$.

2. A composition as set forth in claim 1 wherein the metal hydroxide is selected from the group consisting of ferrous hydroxide, ferric hydroxide and stannous hydroxide.

3. A composition as set forth in claim 1 wherein the radionuclide is selected from the group consisting of technetium-99m and iron-59.

* * * * *